US00PP29930P3

(12) United States Plant Patent
Olesen

(10) Patent No.: US PP29,930 P3
(45) Date of Patent: Dec. 4, 2018

(54) MINIATURE ROSE PLANT NAMED 'POULTY022'

(50) Latin Name: ***Rosa* hybrid**
Varietal Denomination: Poulty022

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 51 days.

(21) Appl. No.: 15/330,285

(22) Filed: Sep. 6, 2016

(65) Prior Publication Data

US 2018/0070497 P1 Mar. 8, 2018

(51) Int. Cl.
*A01H 5/02* (2018.01)
*A01H 6/74* (2018.01)

(52) U.S. Cl.
USPC ..... Plt./119
CPC ..... *A01H 5/02* (2013.01); *A01H 6/749* (2018.05)

(58) Field of Classification Search
USPC ..... Plt./119
See application file for complete search history.

(56) References Cited

PUBLICATIONS

Perfection by Poulsen, Oct. 2013.*

* cited by examiner

*Primary Examiner* — Keith O. Robinson

(57) ABSTRACT

A new garden rose plant of the Miniature class which has abundant, yellow-orange flowers and attractive foliage. This new and distinct variety has shown to be uniform and stable in the resulting generations from asexual propagation.

3 Drawing Sheets

Botanical designation: *Rosa* hybrid.
Variety denomination: 'Poulty022'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulty022', originated as a single seedling from the stated cross.

The new variety may be distinguished from its male pollen parent and female seed parent primarily by the following characteristics. The male pollen plant has apricot colored flowers. The female seed parent has yellow flowers.

The objective of the hybridization of this rose variety was to create a new and distinct variety for garden use with unique qualities, such as:

1. Uniform and abundant yellow-orange flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulty022' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulty022' was selected in the spring of 2011 by the inventor as a single plant from the progeny of the aforementioned hybridization.

Asexual reproduction of 'Poulty022' by rooted cuttings was first done by Mogens N. Olesen in the nursery in Fredensborg, Denmark in July, 2011. This initial and other subsequent asexual propagations conducted in controlled environments have demonstrated that the characteristics of 'Poulty022' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty022'.

Specifically illustrated in FIG. 1 of the drawings are petals detached, flowers at various stages of opening, flower bud, sepals detached, and reproductive flower parts.

Figure 1:
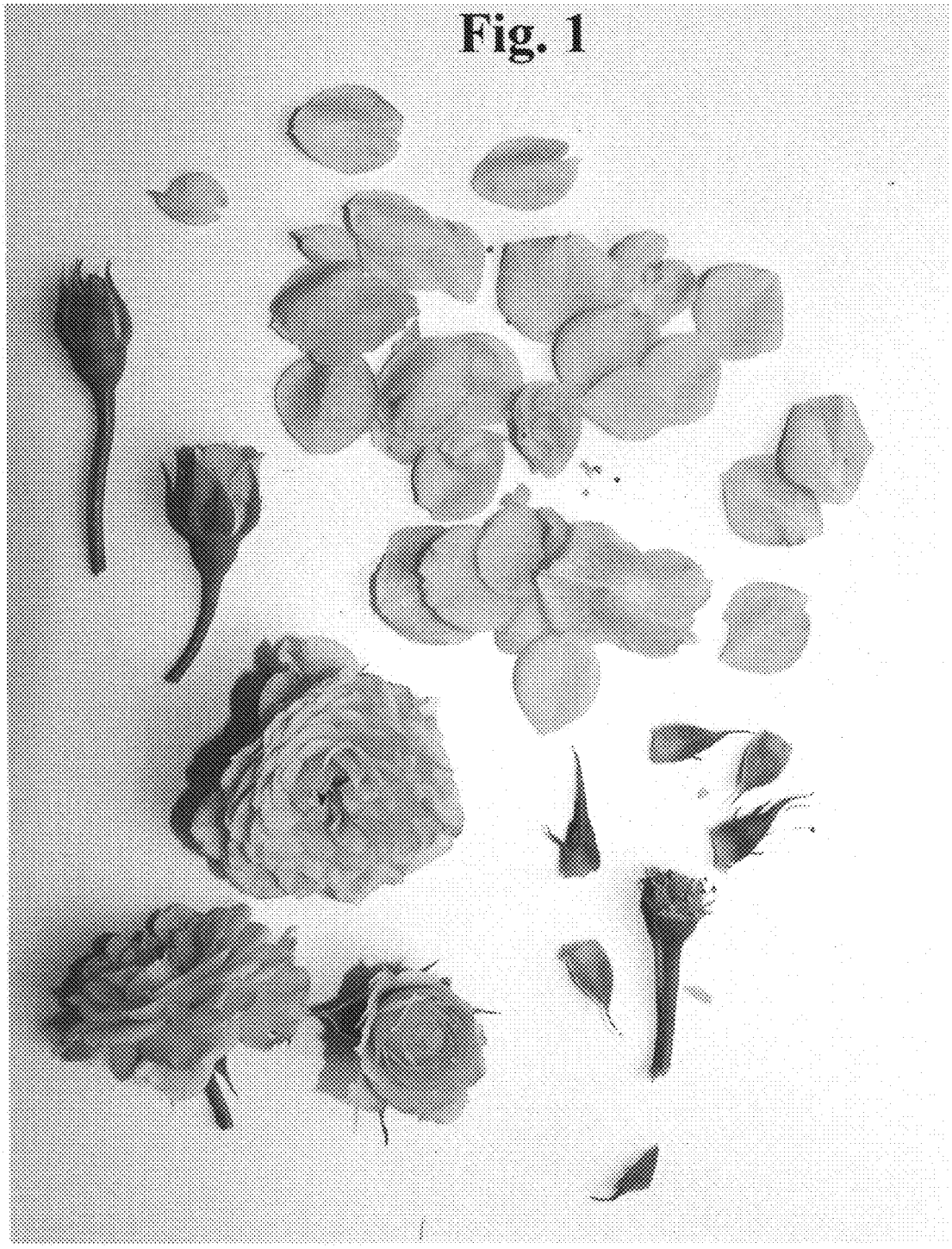
Figure 2:
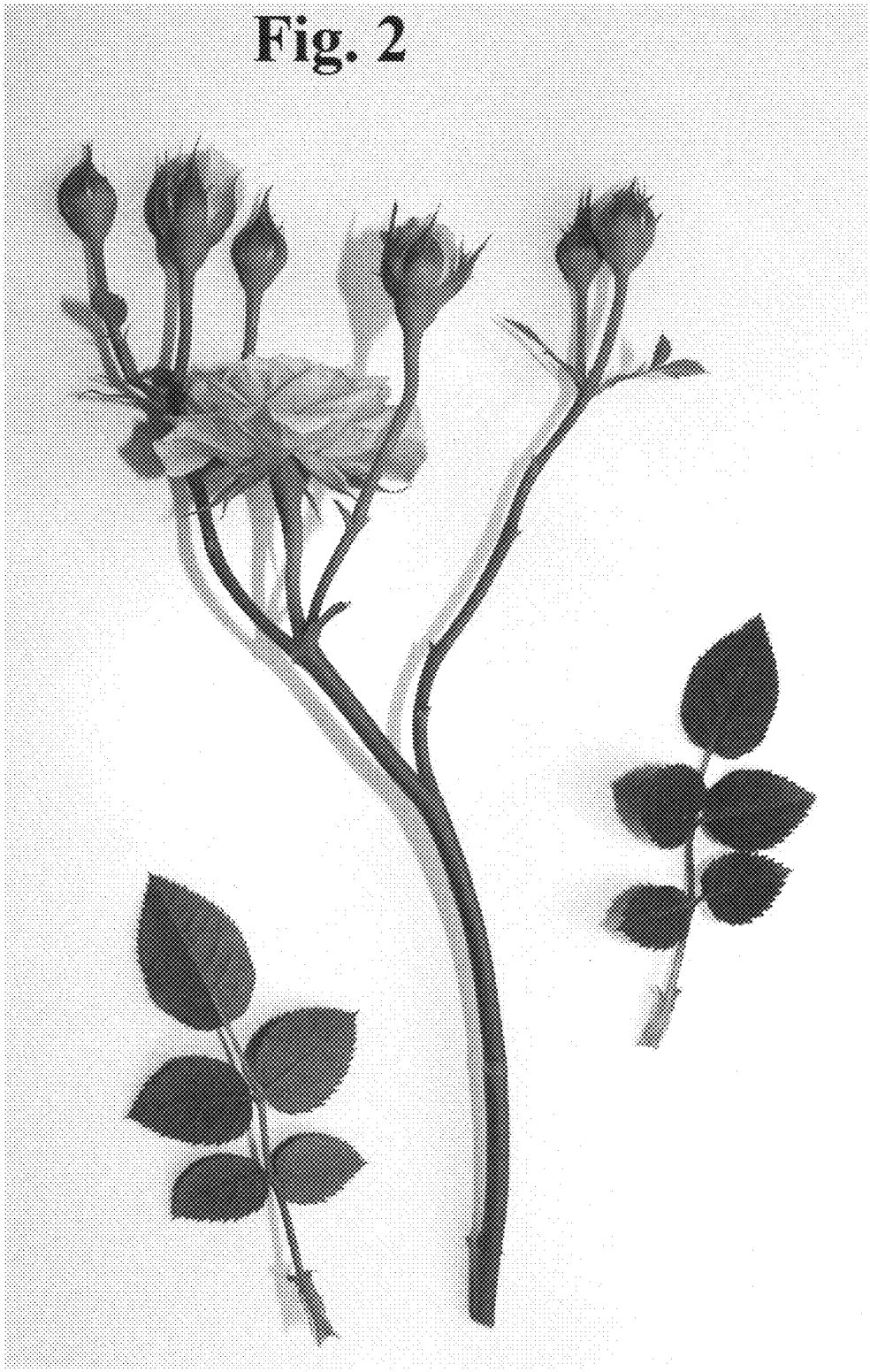

Specifically illustrated in FIG. 2 is a flowering branch and leaves.

Figure 3:
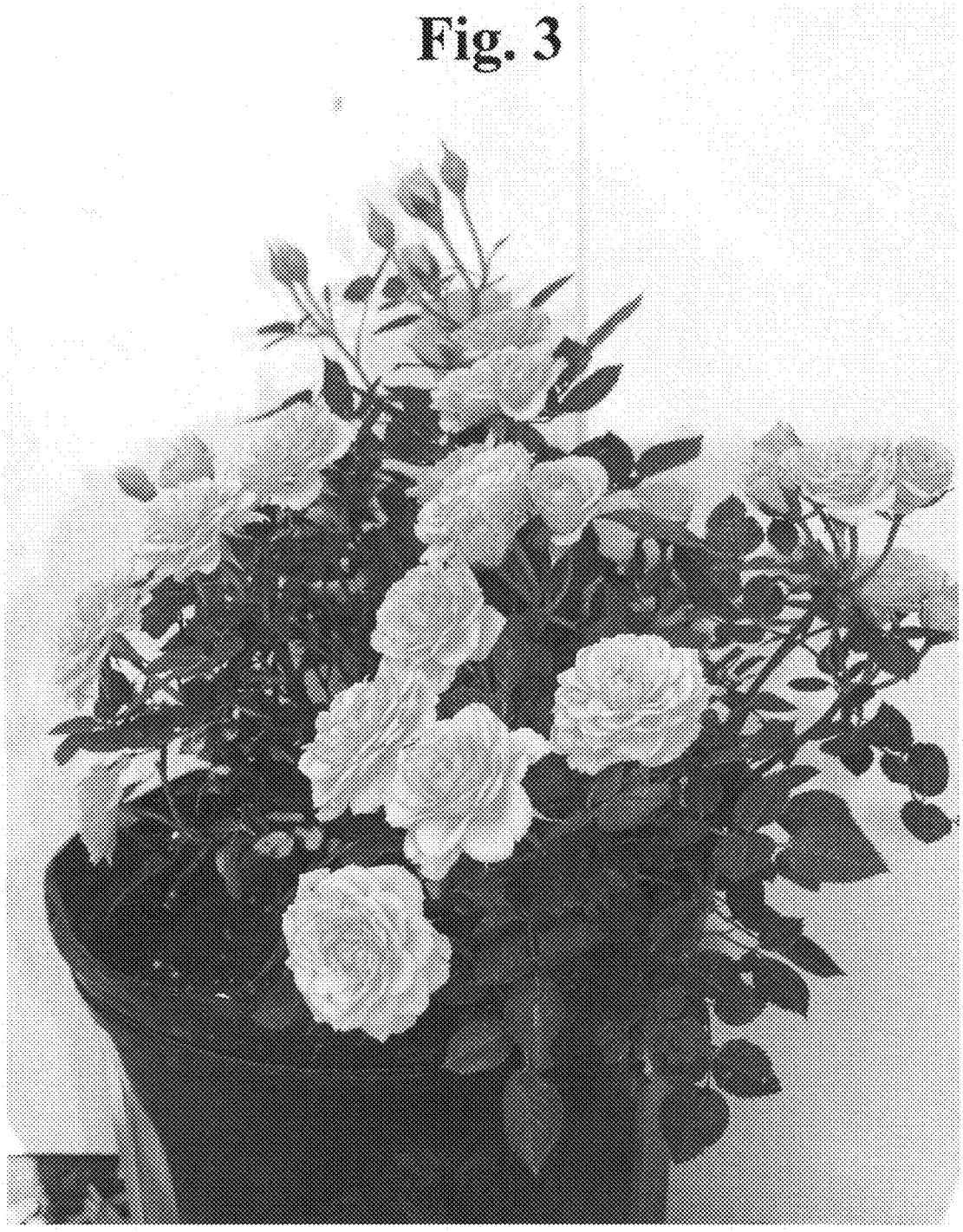

Specifically illustrated in FIG. 3 is the entire plant in flower. Plants shown are 2 years of age.

DETAILED DESCRIPTION OF THE VARIETY

The following is a description of 'Poulty022', as observed in its growth in a 2 gallon container in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulmist', U.S. Plant Pat. No. 18,975 are compared to 'Poulty022' in Chart 1.

CHART 1

| | 'Poulty022' | 'Poulmist' |
|---|---|---|
| Petal Count | 60 | 35 to 40 |
| Flower Diameter | 45 mm | 40 mm |
| General Tonality of Flower Color | Yellow-Orange Group 15B | Yellow Group 12B |

FLOWER AND FLOWER BUD

Blooming habit: Continuous.

Flower bud:

*Size.*—Upon opening, 20 mm in length from base of receptacle to end of bud. Bud diameter is 10 mm.

*Bud form.*—Ovoid.

*Bud color.*—As sepals divide petals are Yellow Group 11B with intonations of Orange-Red Group N34D.

*Sepal inner surface.*—Color: Yellow-Green Group 147A. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 mm long; 7 mm wide.

*Receptacle.*—Texture: Smooth. Size: 4 mm in height by 7 mm wide. Color: Yellow-Green Group 144A. Shape: Campanulate.

*Pedicel.*—Surface: Smooth. Length: 24 mm. Diameter: 2 mm on average. Color: Yellow-Green Group 144A. Strength: Strong.

*Peduncle.*—Length: 40 to 70 mm. Diameter: About 3 mm. Color: Yellow-Green Group 145A. Texture: Smooth.

Flower bud development: Flower buds are borne in clusters of 5 to 7 flower buds per stem.

Flower bloom:

*Fragrance.*—None.

*Duration.*—The blooms have a duration on the plant of approximately 28 days. Petals do not fall cleanly away from plant after flowers have fully matured.

*Size.*—Flower diameter is 45 mm when open. Flower depth is 15 mm.

*Flower shape.*—Rosette. Very double flower with many slightly overlapping petals of different sizes.

*Shape of flower, side view.*—The upper portion is concave. The lower portion is convex.

Petalage: Under normal conditions, flowers have 60 petals total.

General tonality of flower: Open flowers are Yellow-Orange Group 15B.

Petal color:

*Upon opening, outer petals.*—Upper surface: Yellow Group 12B. Lower surface: Orange-Red Group 32B on outermost petals. Other petals are Yellow Group 13B with light splashes of Orange-Red Group N34D.

*Upon opening, inner petals.*—Upper surface: Yellow Group 12B. Lower surface: Yellow Group 13B.

*Basal petal spots, upon opening.*—No distinctive coloration at the petal base observed.

*After opening, outer petals.*—Upper surface: Yellow Group 11B. Lower surface: Yellow Group 11B with intonations of Red Group 48A.

*After opening, inner petals.*—Upper surface: Yellow Group 11B. Lower surface: Yellow Group 11B.

*Basal petal spots, after opening.*—No distinctive coloration at the petal base observed.

Petals:

*Petal reflex.*—Reflexed.

*Margin.*—Mostly entire and uniform. Occasionally a cleft at the margin apes. No undulations.

*Shape.*—Generally rounded. Apex shape: Rounded. Base shape: Acute.

*Size.*—20 mm (l)×16 mm (w).

*Texture.*—Smooth.

*Thickness.*—Average.

Petaloids:

*Size.*—15 mm (l) by 6 mm (w).

*Quantity.*—About 5.

*Shape.*—Elliptic, with an acute base and rounded apex.

*Color.*—Upper surface is Yellow Group 12B. The undersurface is Yellow Group 13B.

Reproductive flower parts:

*Pollen.*—None observed.

*Anthers.*—Size: 1 mm in length. Color: Greyed-Orange Group 163A. Quantity: 45 on average.

*Filaments.*—Color: Yellow-Orange Group 17A. Length: 3 mm.

*Pistils.*—Length: 4 mm. Quantity: 30 on average.

*Stigmas.*—Color: Greyed-Yellow Group 160A.

*Styles.*—Color: Yellow-Green Group 149D.

*Location of stigmas.*—Level location relative to the length of the filaments and the height of the anthers.

*Hips.*—None Observed.

PLANT

Plant growth: Upright, bushy. Plants are 20 cm in height, and 20 cm wide.

Stems:

*Color.*—Juvenile growth: Yellow-Green Group 144B. Mature growth: Yellow-Green Group 144A.

*Length.*—On average, canes are 10 cm from the base of the plant to the flowering portion.

*Diameter.*—5 mm.

*Internodes.*—On mature canes about 40 mm between nodes.

*Surface texture.*—Young wood: Smooth. Older wood: Smooth.

Long prickles: None observed.

Plant foliage:

*Compound leaf.*—95 mm (l)×54 mm (w).

*Quantity.*—About 2 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 146B.

Plant leaves and leaflets:

*Stipules*.—Size: 9 mm long, 3 mm wide. Quantity: 2 per compound leaf. Shape: Linear, slightly broad based with outward extending apices. Margins: Finely serrated. Color:

*Petiole*.—Length: 30 mm. Diameter: 2 mm.

*Upper surface*.—Color: Yellow-Green Group 144A.

*Lower surface*.—Color: Yellow-Green Group 144A.

*Rachis*.—Length: 30 mm. Upper surface: Color: Yellow-Green Group 144A.

*Lower surface*.—Color: Yellow-Green Group 144A.

*Leaflet*.—Quantity: Normally 5 leaflets. Margins: Serrated. Size: On average terminal leaflets are 32 mm long, 20 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulty022', substantially as illustrated and described herein, due to its abundant yellow-orange flowers, disease resistance, and extended period of bloom.

* * * * *